United States Patent
Sakaue et al.

(10) Patent No.: US 8,409,869 B2
(45) Date of Patent: Apr. 2, 2013

(54) HYDROGEN SENSOR, HYDROGEN DETECTING SYSTEM AND METHOD

(75) Inventors: Hirotaka Sakaue, Tokyo (JP); Chih-Yung Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 233 days.

(21) Appl. No.: 13/076,275

(22) Filed: Mar. 30, 2011

(65) Prior Publication Data

US 2012/0040469 A1   Feb. 16, 2012

(30) Foreign Application Priority Data

Aug. 13, 2010  (TW) .............................. 99127103 A

(51) Int. Cl.
*G01N 21/76*      (2006.01)
(52) U.S. Cl. ..................... 436/172; 436/144; 422/82.08; 422/91
(58) Field of Classification Search ............... 422/82.08, 422/91
See application file for complete search history.

(56) References Cited

U.S. PATENT DOCUMENTS 6,596,236 B2 *  7/2003  DiMeo et al. .................. 422/88

* cited by examiner

*Primary Examiner* — Robert Xu
(74) *Attorney, Agent, or Firm* — Christie, Parker & Hale, LLP

(57) ABSTRACT

A hydrogen sensor comprises a substrate having a surface coated with a hydrogen absorbing material and a temperature sensitive luminophore such that when the temperature sensitive luminophore is excited, it generates a fluorescent light, the luminescence of which is changed by an exothermic heat resulting from the adsorption of hydrogen through the hydrogen absorbing material. A hydrogen detecting system and a method of detecting hydrogen using the hydrogen sensor are also disclosed.

13 Claims, 4 Drawing Sheets

HYDROGEN SENSOR, HYDROGEN DETECTING SYSTEM AND METHOD

CROSS-REFERENCE TO RELATED APPLICATION

This application claims priority of Taiwanese Patent Application No. 099127103 filed on Aug. 13, 2010.

BACKGROUND OF THE INVENTION

1. Field of the Invention

The invention relates to a hydrogen sensor, and hydrogen detecting system and method.

2. Description of the Related Art $H_2$ has been used to generate electricity in a fuel cell or a rocket propellant. Great care must be taken to store $H_2$ because it is flammable and potentially explosive. Various $H_2$ sensors have been proposed to detect $H_2$ content of a gas in a storage system. A conventional $H_2$ sensor normally includes an absorbing medium that can selectively attract or absorb $H_2$. Several $H_2$ absorbing mediums have been proposed in the art. One of the $H_2$ absorbing mediums is a palladium coated substrate that has been widely used to absorb $H_2$ for detection of the $H_2$ content in a gas. Palladium (Pd) can react with $H_2$ to form palladium hydride. The reaction is reversible. Since Pd and palladium hydride have different optical properties, such as reflectivity, the reflectance of a Pd coated substrate changes when $H_2$ is adsorbed and/or absorbed on the Pd coated substrate. Hence, by measuring a change in intensity of the reflectance of the Pd coated substrate, the content of $H_2$ can be determined. For the same $H_2$ content, the higher the intensity change of the reflectance, the higher will be the sensitivity of the $H_2$ sensor.

SUMMARY OF THE INVENTION

The object of the present invention is to provide a hydrogen sensor with a higher sensitivity in detecting hydrogen than the conventional hydrogen sensor.

Another object of this invention is to provide a hydrogen detecting system and method.

According to one aspect of the present invention, there is provided a hydrogen sensor that comprises a substrate having a surface coated with a hydrogen absorbing material and a temperature sensitive luminophore such that, when the temperature sensitive luminophore is excited, it generates a fluorescent light, the luminescence of which is changed by an exothermic heat resulting from an interaction of the hydrogen absorbing material with hydrogen.

According to another aspect of the present invention, there is provided a hydrogen detecting system that comprises: a hydrogen sensor having a substrate with a surface coated with a hydrogen absorbing material and a temperature sensitive luminophore; a light source for exciting the temperature sensitive luminophore on the substrate so as to generate a fluorescent light; and a photo-detector for monitoring the luminescence of the fluorescent light generated from the temperature sensitive luminophore. When the hydrogen sensor is exposed to a hydrogen-containing gas, the hydrogen absorbing material interacts with hydrogen to generate heat, which results in a change in luminescence of the fluorescent light, thereby permitting detection of hydrogen in the hydrogen-containing gas.

According to yet another aspect of the present invention, there is provided a method of detecting hydrogen. The method comprises: preparing a hydrogen sensor having a substrate with a surface coated with a hydrogen absorbing material and a temperature sensitive luminophore; irradiating the surface of the substrate so as to excite the temperature sensitive luminophore on the substrate to generate a fluorescent light; exposing the surface of the substrate to a hydrogen-containing gas for a predetermined time to permit the hydrogen absorbing material to interact with hydrogen and to generate heat thereby; and monitoring a change in luminescence of the fluorescent light due to the heat resulting from an interaction of the hydrogen absorbing material and hydrogen.

BRIEF DESCRIPTION OF THE DRAWINGS

In drawings which illustrate an embodiment of the invention.

DETAILED DESCRIPTION OF THE PREFERRED EMBODIMENTS

Figure 1:
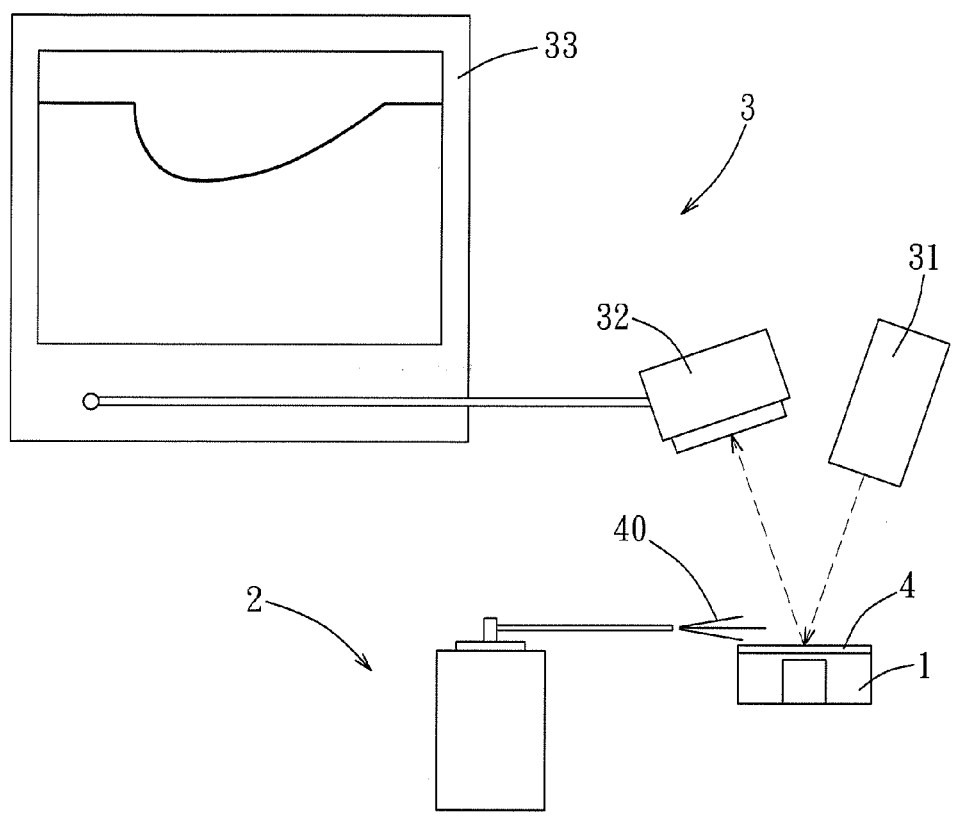
FIG. 1 is a schematic view of the preferred embodiment of a hydrogen detecting system according to this invention.
Figure 2:
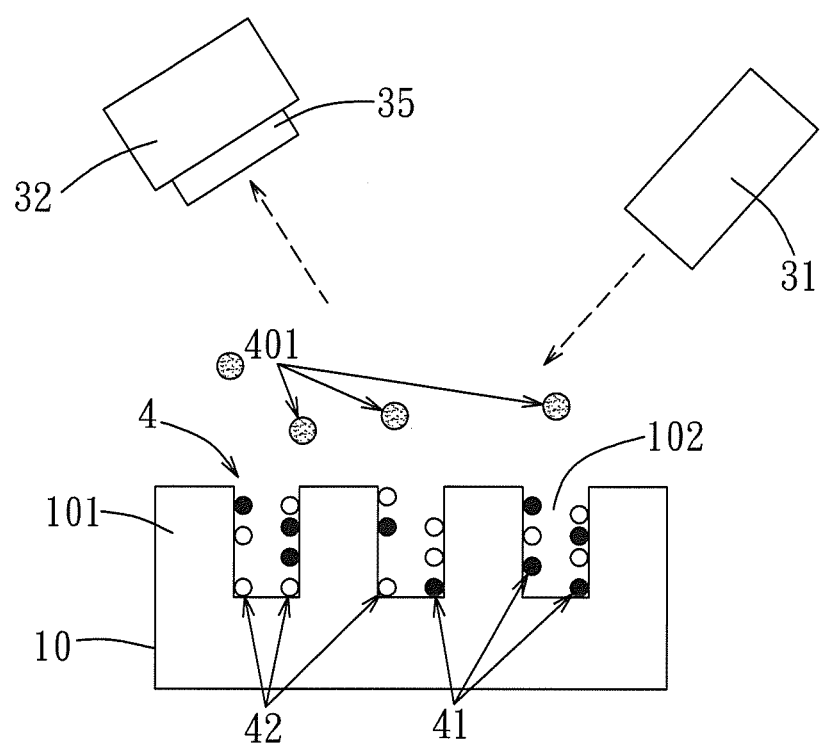
FIG. 2 is a schematic view illustrating the structure of a hydrogen sensor of the preferred embodiment.

FIGS. 1 and 2 illustrate the preferred embodiment of a hydrogen detecting system that includes: a sensor support 1, a hydrogen sensor 4 disposed on the sensor support 1 and having a substrate 10 with a porous surface 101 coated with a hydrogen absorbing material 41 and a temperature sensitive luminophore 42 thereon; a light source 31 for exciting the temperature sensitive luminophore 42 on the substrate 10 so as to generate a fluorescent light; a photo-detector 32, such as a photo-multiplier tube (PMT), for monitoring the luminescence of the fluorescent light generated from the temperature sensitive luminophore 42 through a band-pass filter 35, the photo-multiplier tube 32 receiving the fluorescent light and converting it into an electrical signal; and an output means 33, such as an oscilloscope, for outputting signals. The output means 33 converts the electrical signal into readable information, such as a time-resolved and intensity-based diagram. When the hydrogen sensor 4 is exposed to a hydrogen-containing gas 40 sprayed from a gas sprayer 2, the hydrogen absorbing material 41 absorbs and/or adsorbs hydrogen 401 in the hydrogen-containing gas 40, which results in generation of an exothermic heat, which, in turn, results in a reduction in luminescence of the fluorescent light, thereby permitting detection of hydrogen 401 in the hydrogen-containing gas.

The porous surface 101 of the substrate 10 is formed with a plurality of pores 102. The hydrogen absorbing material 41 and the temperature sensitive luminophore 42 are disposed in each of the pores 102.

In this embodiment, the light source 31 includes a UV light emitting diode array (not shown).

Preferably, the hydrogen absorbing material 41 is selected from platinum, palladium, nickel, lanthanum, aluminum, and combinations thereof, and more preferably, the hydrogen absorbing material 41 is palladium.

Preferably, the temperature sensitive luminophore is selected from europium(III) thenoyltrifluoroacetonate (EuTTA), N,N'-bis (2,5-di-tert-butylphenyl)-3,4,9,10-perylene dicarboximide, palladium(II) octaethyl porphyrin, tris(2,2'-bipyridyl) ruthenium(II) chloride hexahydrate, coumarin 1, Rhodamine B, sulpho rhodamine B, rose bengal, pyronin B, pyronin Y, and quinizarin, and more preferably, the temperature sensitive luminophore is europium(III) thenoyl-trifluoroacetonate.

The hydrogen sensor 4 of this invention is preferably prepared by dipping the substrate 10 coated with the hydrogen absorbing material 41 into a luminophore solution containing a solvent and the temperature sensitive luminophore 42 which is dissolved in the solvent for deposition of the temperature sensitive luminophore 42 on the substrate 10, followed by drying to remove the solvent from the substrate 10.

Preferably, the solvent is selected from hexane, toluene, dichloroform, and acetone, and more preferably, the solvent is hexane.

Figure 3:
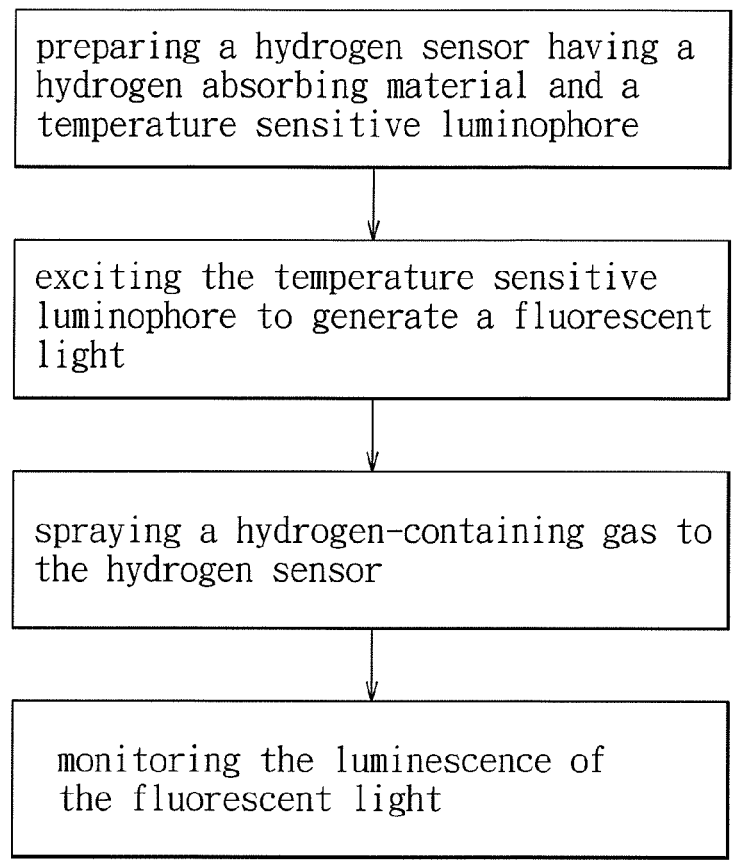
FIG. 3 is a flow chart of the preferred embodiment of a method of detecting hydrogen according to this invention.

Referring to FIG. 3, in combination with FIGS. 1 and 2, the method of detecting hydrogen includes the steps of: preparing the hydrogen sensor 4; irradiating the porous surface 101 of the substrate 10 using the light source 31 to excite the temperature sensitive luminophore 42 on the substrate 10 to generate a fluorescent light; exposing the surface 101 of the substrate 10 to the hydrogen-containing gas 40 by spraying the hydrogen-containing gas 40 directly on the surface 101 of the substrate 10 for a predetermined time using the gas sprayer 2 to permit the hydrogen absorbing material 41 to absorb and/or adsorb hydrogen 401 and to generate heat thereby; and monitoring the luminescence of the fluorescent light using the photo-detector 32 and outputting signals using the output means 33.

Figure 4:
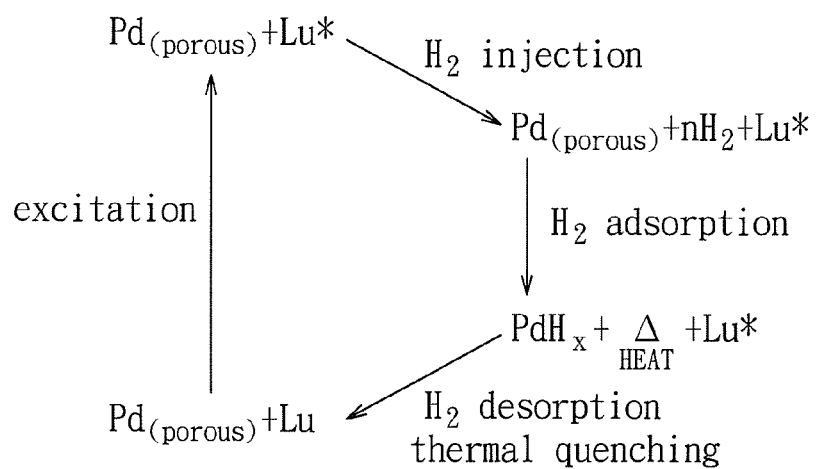
FIG. 4 is a schematic view illustrating a mechanism including a photophysical process, an adsorption process, a thermal quenching process, and a desorption process which concurrently occur during irradiation and adsorption of hydrogen on the hydrogen sensor of the preferred embodiment.

Referring to FIG. 4, in combination with FIGS. 1 and 2, when the hydrogen sensor 4 is exposed to the UV light and the hydrogen-containing gas 40 is sprayed onto the surface 101 of the substrate 10, the hydrogen sensor undergoes a mechanism including a photophysical process, an adsorption process, a thermal quenching process, and a desorption process. In the photophysical process, the temperature sensitive luminophore 42 (the term "Lu" indicated in FIG. 4 represents a non-excited state of the temperature sensitive luminophore 42) is exited by the UV light (the term "Lu*" indicated in FIG. 4 represents an excited state of the temperature sensitive luminophore 42). In the adsorption process, the hydrogen absorbing material 41 (represented by the term "Pd" in FIG. 4) undergoes exothermic reaction with hydrogen to form a hydride of the hydrogen absorbing material 41 (represented by the term "PdH$_x$" in FIG. 4), which results in generation of exothermic heat. In the thermal quenching process and the desorption process, the excited temperature sensitive luminophore 42 is thermally quenched by the exothermic heat liberation and returns to the non-excited state, and the hydride of the hydrogen absorbing material 41 undergoes desorption and returns to the non-hydride form.

The following Example and Comparative Examples are provided to illustrate the merits of the preferred embodiment of the invention, and should not be construed as limiting the scope of the invention.

Example 1 (E1)

Preparation of the Hydrogen Sensor

A porous substrate was dipped in a solution containing Pd for deposition of Pd on the porous substrate. EuTTA was dissolved in hexane to form a luminophore solution having a EuTTA concentration of 10 μM. The Pd coated substrate was dipped in the luminophore solution for deposition of EuTTA on the porous substrate, followed by drying so as to form a hydrogen sensor.

Performance Test

The hydrogen sensor thus formed was exposed to a UV light having a wavelength of 375 nm using a UV light emitting diode array so as to excite EuTTA to generate a fluorescent light. A photo-multiplier tube was used to monitor the luminescence of the fluorescent light through a band-pass filter having a transmittance bandpass range of 620 nm±50 nm. A hydrogen-containing gas (In this Example, a substantially pure hydrogen greater than 99% was used as the hydrogen-containing gas. The hydrogen percentage was determined based on the partial pressure of hydrogen) was sprayed onto the hydrogen sensor for 5 seconds. The intensity of the fluorescent light was recorded and the intensity change percentage of the fluorescent light was determined using an oscilloscope before and after spraying of the hydrogen-containing gas. The intensity change percentage of the fluorescent light is defined as:

$$\frac{\text{Intensity of fluorescent light after spraying}}{\text{Intensity of fluorescent light before spraying}} \times 100$$

Figure 5:
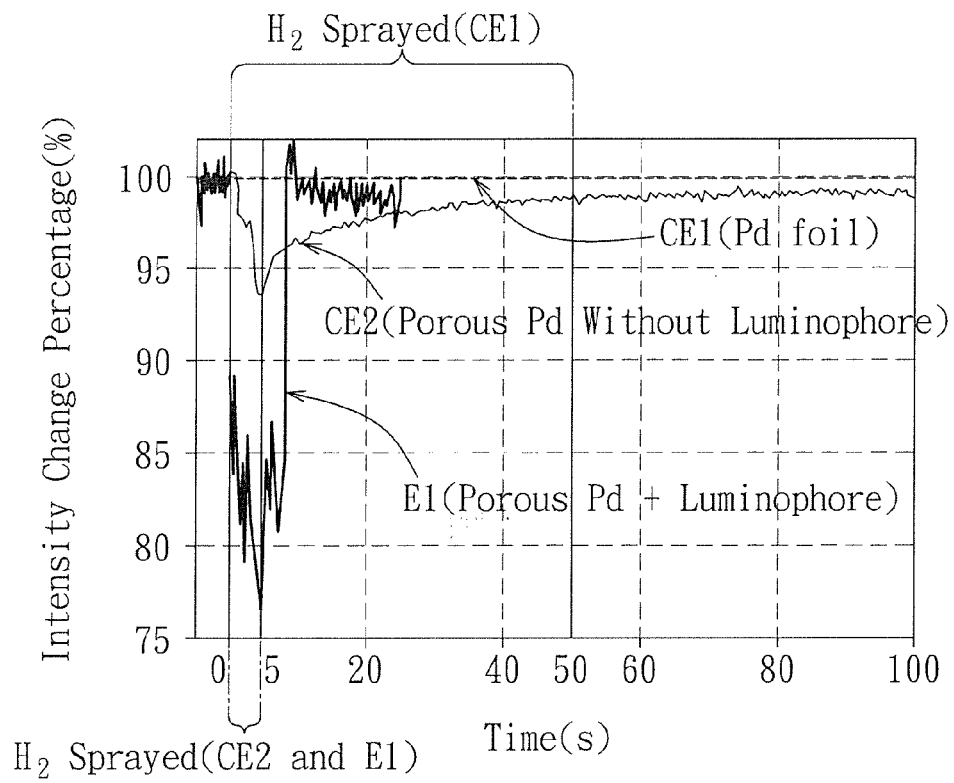
FIG. 5 is a diagram showing three plots including the intensity change percentage of the reflectance of a surface of a Pd foil on a substrate (Comparative Example 1), the intensity change percentage of the reflectance of a porous surface of a substrate coated with Pd (Comparative Example 2), and the intensity change percentage of a fluorescent light generated from a temperature sensitive luminophore on a porous surface of a substrate of the hydrogen sensor of the preferred embodiment (Example 1) before and after spraying of hydrogen.

The results of the intensity change percentage (E1) of the fluorescent light is shown in FIG. 5. A 24% intensity change is achieved between the beginning and the end of spraying hydrogen (i.e., the spraying time is 5 seconds).

Comparative Example 1 (CE1)

Preparation of the Hydrogen Sensor

A Pd foil was attached to a substrate so as to form the hydrogen sensor of Comparative Example 1.

Performance Test

The hydrogen sensor thus formed was exposed to a red laser beam. A photo-multiplier tube was used to monitor the reflectance of the laser beam from the hydrogen sensor. The hydrogen-containing gas employed in Example 1 was sprayed onto the hydrogen sensor for 50 seconds. The intensity of the reflectance of the laser beam was recorded and the intensity change percentage of the reflectance was determined using an oscilloscope before and after spraying of the hydrogen-containing gas. The intensity change percentage of the reflectance is defined as:

$$\frac{\text{Intensity of reflectance after spraying}}{\text{Intensity of reflectance before spraying}} \times 100$$

The results of the intensity change percentage (CE1) of the reflectance of the laser beam is shown in FIG. 5. A 0.3% intensity change is obtained between the beginning and the end of spraying hydrogen (i.e., the spraying time is 50 seconds).

Comparative Example 2 (CE2)

Preparation of the Hydrogen Sensor

The hydrogen sensor of Comparative Example 2 has a structure similar to that of the hydrogen sensor of Example 1 except that the hydrogen sensor of Comparative Example 2 is not coated with the temperature sensitive luminophore.

Performance Test

The hydrogen sensor thus formed was exposed to a red laser beam. A photo-multiplier tube was used to monitor the reflectance of the laser beam from the hydrogen sensor. The hydrogen-containing gas employed in Example 1 was sprayed onto the hydrogen sensor for 5 seconds. The intensity of the reflectance of the laser beam was recorded and the intensity change percentage of the reflectance was determined using an oscilloscope before and after spraying of the hydrogen-containing gas. The results of the intensity change percentage (CE2) of the reflectance of the laser beam is shown in FIG. 5. A 7% intensity change is obtained between the beginning and the end of spraying hydrogen (i.e., the spraying time is 5 seconds).

The results of the performance test of Example 1 and Comparative Examples 1 and 2 demonstrate that the hydrogen sensor of Example 1 has a much higher intensity change percentage, i.e., a much higher sensitivity, than those of Comparative Examples 1 and 2.

Figure 6:
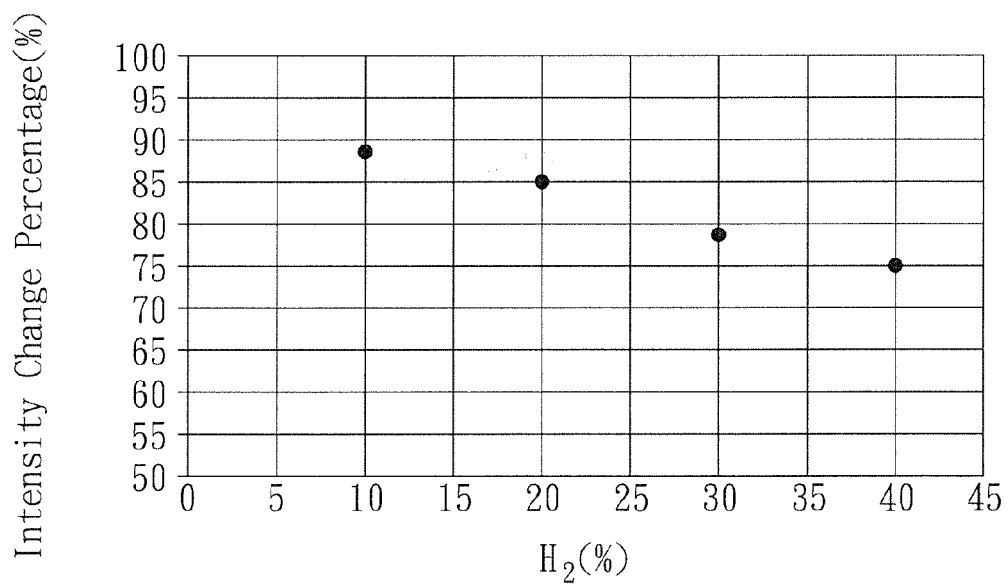
FIG. 6 is a diagram showing the intensity change of the fluorescent light of the hydrogen sensor of the preferred embodiment at the end of spraying of hydrogen for different hydrogen contents.

FIG. 6 shows the intensity changes of the fluorescent light at the end of spraying hydrogen (the spraying time is about 12 seconds) to the hydrogen sensor of Example 1 for different hydrogen concentrations, i.e., 10%, 20%, 30% and 40%, respectively. Each of the hydrogen percentages was determined based on the partial pressure of hydrogen. The results show that the higher the hydrogen concentration in the hydrogen-containing gas, the higher the intensity change of the fluorescent light.

By incorporating the hydrogen absorbing material 41 and the temperature sensitive luminophore 42 into the porous surface 101 of the substrate 10, the hydrogen sensor 4 thus formed can achieved a higher sensitivity in detecting hydrogen as compared to those of the conventional hydrogen sensors.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A hydrogen sensor comprising:
a substrate having a surface coated with a hydrogen absorbing material and a temperature sensitive luminophore such that when said temperature sensitive luminophore is excited, it generates a fluorescent light, the luminescence of which is changed by an exothermic heat resulting from an interaction of said hydrogen absorbing material with hydrogen.

2. The hydrogen sensor of claim 1, wherein said surface of said substrate is porous and is formed with a plurality of pores.

3. The hydrogen sensor of claim 1, wherein said hydrogen absorbing material is selected from platinum, palladium, nickel, lanthanum, aluminum, and combinations thereof.

4. The hydrogen sensor of claim 3, wherein said hydrogen absorbing material is palladium.

5. The hydrogen sensor of claim 1, wherein said temperature sensitive luminophore is selected from europium(III) thenoyltrifluoroacetonate, N,N'-bis (2,5-di-tert-butylphenyl)-3,4,9,10-perylene dicarboximide, palladium(II) octaethyl porphyrin, tris(2,2'-bipyridyl) ruthenium(II) chloride hexahydrate, coumarin 1, Rhodamine B, sulpho rhodamine B, rose bengal, pyronin B, pyronin Y, and quinizarin.

6. The hydrogen sensor of claim 5, wherein said temperature sensitive luminophore is europium(III) thenoyltrifluoroacetonate.

7. A hydrogen detecting system comprising:
a hydrogen sensor having a substrate with a surface coated with a hydrogen absorbing material and a temperature sensitive luminophore;
a light source for exciting the temperature sensitive luminophore on the substrate so as to generate a fluorescent light; and
a photo-detector for monitoring the luminescence of the fluorescent light generated from the temperature sensitive luminophore;
wherein when the hydrogen sensor is exposed to a hydrogen-containing gas, the hydrogen absorbing material interacts with hydrogen and generate heat, which results in a change in luminescence of the fluorescent light, thereby permitting detection of hydrogen in the gas.

8. The hydrogen detecting system of claim 7, wherein the temperature sensitive luminophore is europium(III) thenoyltrifluoroacetonate.

9. The hydrogen detecting system of claim 8, wherein the light source includes a UV light emitting diode array.

10. The hydrogen detecting system of claim 7, further comprising a gas sprayer for spraying a hydrogen-containing gas onto the hydrogen sensor.

11. A method of detecting hydrogen, comprising:
preparing a hydrogen sensor having a substrate with a surface coated with a hydrogen absorbing material and a temperature sensitive luminophore;
irradiating the surface of the substrate to excite the temperature sensitive luminophore on the substrate to generate a fluorescent light;
exposing the surface of the substrate to a hydrogen-containing gas for a predetermined time so as to permit the hydrogen absorbing material to interact with hydrogen and to generate heat thereby; and
monitoring a change in luminescence of the fluorescent light in response to the heat resulting from the interaction of the hydrogen absorbing material and hydrogen.

12. The method of claim 11, wherein the hydrogen sensor is prepared by dipping the substrate coated with the hydrogen absorbing material into a luminophore solution containing a solvent and the temperature sensitive luminophore dissolved in the solvent, the solvent being selected from hexane, toluene, dichloroform, and acetone.

13. The method of claim 11, wherein the solvent is hexane.

* * * * *